United States Patent
Ross

(10) Patent No.: US 10,292,640 B2
(45) Date of Patent: May 21, 2019

(54) EVALUATION OF PAIN IN HUMANS

(71) Applicant: David B. Ross, Southwest Ranches, FL (US)

(72) Inventor: David B. Ross, Southwest Ranches, FL (US)

( * ) Notice: Subject to any disclaimer, the term of this patent is extended or adjusted under 35 U.S.C. 154(b) by 303 days.

(21) Appl. No.: 14/576,120

(22) Filed: Dec. 18, 2014

(65) Prior Publication Data
US 2015/0105688 A1    Apr. 16, 2015

Related U.S. Application Data

(63) Continuation of application No. 11/204,507, filed on Aug. 17, 2005, now abandoned.

(51) Int. Cl.
*A61B 5/00* (2006.01)
*G06F 19/00* (2018.01)

(52) U.S. Cl.
CPC .............. *A61B 5/4824* (2013.01); *A61B 5/00* (2013.01); *A61B 5/0053* (2013.01); *A61B 5/0057* (2013.01); *A61B 5/4035* (2013.01); *G06F 19/00* (2013.01); *A61B 5/4519* (2013.01); *A61B 5/4528* (2013.01)

(58) Field of Classification Search
CPC ......... A61B 6/4824; A61B 6/483; A61B 5/00; A61B 5/0053; A61B 5/0057; A61B 5/4035; A61B 5/4519; A61B 5/4528
See application file for complete search history.

(56) References Cited

U.S. PATENT DOCUMENTS 7,206,632 B2 *  4/2007  King .................. A61N 1/36021
                                                    600/544

* cited by examiner

*Primary Examiner* — Amanda K Hulbert
(74) *Attorney, Agent, or Firm* — Christopher J. VanDam, PA; Chris Vandam

(57) ABSTRACT

A method for evaluating pain experienced by a human is disclosed. The method includes applying a first noxious stimulus to a normative site on the human, wherein the first noxious stimulus is applied below a pain threshold of the human and logging a first information associated with the first noxious stimulus. The method further includes applying a second noxious stimulus to a source of the pain in the human, wherein the second noxious stimulus is applied until pain threshold is reached and logging a second information associated with the second noxious stimulus. The method further includes increasing the second noxious stimulus until pain tolerance is reached and logging a third information associated with the second noxious stimulus. The method further includes continuing to apply the second noxious stimulus until the human can no longer tolerate the second noxious stimulus and logging a fourth information associated with the second noxious stimulus.

14 Claims, 5 Drawing Sheets

| 502 ↘ Trial 1 | 551 Time | 552 Angle | 553 EMG1 | 554 EMG2 | 555 SCL | 556 SCR | 557 Pulse | 558 Pulse Pressure |
|---|---|---|---|---|---|---|---|---|
| 511 Baseline | | | | | | | | |
| 512 Pain Threshold | | | | | | | | |
| 513 Pain Tolerance | | | | | | | | |
| 514 Pain Termination | | | | | | | | |
| 515 Rest (25 sec) | | | | | | | | |

| 504 ↘ Trial 2 | Time | Angle | EMG1 | EMG2 | SCL | SCR | Pulse | Pulse Pressure |
|---|---|---|---|---|---|---|---|---|
| 521 Baseline | | | | | | | | |
| 522 Pain Threshold | | | | | | | | |
| 523 Pain Tolerance | | | | | | | | |
| 524 Pain Termination | | | | | | | | |
| 525 Rest (25 sec) | | | | | | | | |

| 506 ↘ Trial 2 | Time | Angle | EMG1 | EMG2 | SCL | SCR | Pulse | Pulse Pressure |
|---|---|---|---|---|---|---|---|---|
| 531 Baseline | | | | | | | | |
| 532 Pain Threshold | | | | | | | | |
| 533 Pain Tolerance | | | | | | | | |
| 534 Pain Termination | | | | | | | | |
| 535 Rest (25 sec) | | | | | | | | |

| 508 ↘ Results (Avg +S D) | Time | Angle | EMG1 | EMG2 | SCL | SCR | Pulse | Pulse Pressure |
|---|---|---|---|---|---|---|---|---|
| 541 Baseline | | | | | | | | |
| 542 Pain Threshold | | | | | | | | |
| 543 Pain Tolerance | | | | | | | | |
| 544 Pain Termination | | | | | | | | |
| 545 Rest (25 sec) | | | | | | | | |

FIG. 5

EVALUATION OF PAIN IN HUMANS

1. CROSS-REFERENCE TO RELATED APPLICATIONS

This application claims priority to U.S. non-provisional patent application Ser. No. 11/204,507 filed Aug. 17, 2005. The aforementioned U.S. non-provisional patent application is hereby incorporated by reference in its entirety.

2. STATEMENT REGARDING FEDERALLY SPONSORED RESEARCH or Development

Not Applicable.

3. FIELD OF THE INVENTION

The invention disclosed broadly relates to the field of medicine, and more particularly relates to the field of pain management.

BACKGROUND OF THE INVENTION

Pain is defined as an unpleasant sensory or emotional experience associated with actual or potential tissue damage. It is epidemic in our country. It is the single most common complaint seen in healthcare. Pain-related prescriptions account for more than one of seven medical prescriptions written each year. The national medical costs alone exceed 100 billion dollars annually. The overall costs are several times greater when social costs of lost productivity, disability indemnity, legal settlements, fraud and other issues are factored into the complex physiologic and/or psychological pain experience. Of the categories of pain, musculoskeletal and neuropathic pains are among the most vexing. These pains often result from alleged injuries where the psychosocial milieu is most intricate. In these settings, questions of etiology, prognosis, treatment, impairment, disability, depression, anxiety, liability, and fraud often coexist. These issues are compounded because the pain complaint is largely subjective and is difficult to assess in an un-biased, qualitative and quantitative fashion.

This problem is made worse when pain becomes chronic. In most circumstances, acute pain is self-limited and will resolve. For example, 80% of all Americans experience low back pain at least once during their lifetime. For the majority, these pain attacks will improve within four weeks to the point that individuals return to their activities (such as work). Twenty-five percent of all lower back injuries persist for more than one month; this minority account for 75% of all healthcare and other expenses related to low back injuries. Each year, 3-4% of the population will be disabled temporarily (largely due to musculoskeletal injury) and 1% of the working-age population is permanently and totally disabled.

The problem is of great national concern. The Joint Commission on Accreditation of Healthcare Organizations (JCAHO) has suggested that pain is the fifth vital sign and should be monitored as vigilantly as blood pressure, pulse, temperature and respiratory rate. Pain, however, is often inadequately evaluated and managed by healthcare professionals because of the complex intermix of components that underlie the individual patient's pain experience. Unlike the other "vital signs [that are quantifiable and unitary]," pain complaints have been difficult to analyze in a pragmatic and cost-effective fashion. Better methodologies are needed to address this national epidemic.

A brief review of the more complete definition of pain offers a starting point to the complex issues involved. According to the International Association of Pain (IASP), pain can be defined as "An unpleasant sensory and emotional experience associated with actual or potential tissue damage, or described in terms of such damage." The subsequent notations add the following clarifications and distinctions:

"Pain is always subjective. Each individual learns the application of the word through experiences related to injury in early life. Biologists recognize that those stimuli which cause pain are liable to damage tissue. Accordingly, pain is that experience we associate with actual or potential tissue damage. It is unquestionably a sensation in a part or parts of the body, but it is also always unpleasant and therefore also an emotional experience. Experiences which resemble pain but are not unpleasant, e.g., pricking, should not be called pain. Unpleasant abnormal experiences (dysesthesias) may also be pain but are not necessarily so because, subjectively, they may not have the usual sensory qualities of pain.

Many people report pain in the absence of tissue damage or any likely pathophysiological cause; usually this happens for psychological reasons. There is usually no way to distinguish their experience from that due to tissue damage if we take the subjective report. If they regard their experience as pain and if they report it in the same ways as pain caused by tissue damage, it should be accepted as pain. This definition avoids tying pain to the stimulus. Activity induced in the nociceptor and nociceptive pathways by a noxious stimulus is not pain, which is always a psychological state, even though we may well appreciate that pain most often has a proximate physical cause."

This definition introduces the problems underlying the proper assessment of the pain experience. A paraphrase of the above yields the following conceptual framework. An individual's pain complaint is always an emotional, psychological experience related to an unpleasant sensation in parts or parts of the body that may occur in the presence or absence of any pathophysiologic (i.e., bioanatomic) cause. One must then factor into the consideration, the known dilemmas of addiction, secondary gain, factitious disorders and malingering. The net result is that an individual's pain complaints can be a complex mixture of pathophysiologic causes, emotional factors, and social components. Each of these domains merits some further discussion.

The pathophysiologic component of the pain experience is the usual focus of the healthcare professional. Using musculoskeletal and peripheral neuropathic pain as the model, the standard medical paradigm seeks to identify the sensitive (i.e., "painful") body region or part and relieve the tissue sensitivity. This is usually attempted using one of several approaches: (a) medications, such as muscle relaxants, anti-inflammatory medications, analgesics, neuropathic pain medications, and others; (b) physical modalities (e.g., physical therapy, chiropractic care, massage, acupuncture, or TENS unit devices); (c) peripheral nerve injections (e.g., anesthesiologic techniques such as nerve blocks, sympathetic ganglia blocks, epidural injections); and (d) surgical techniques (e.g., orthopedic or neurosurgical techniques such as joint surgery, spinal surgery, etc.).

Each of the aforementioned medical approaches is predicated on the notion that there is pathophysiologic tissue sensitivity as the core element underlying the patient's voiced complaint. If the sensitive tissue is properly identified and treated, then the pain complaint will be largely improved. Even a cursory review of the IASP definition of pain quickly demonstrates that the situation cannot be naively reduced to such a singular perspective. In many pain models, the emotional and social domains of the pain experience have been often largely disregarded or ignored during the traditional medical assessment and management of the patient's complaints. The net result is that there has been a both an under- and over-utilization of medical care because of inaccurate or incomplete diagnoses. Two simple statements should suffice to illustrate the point. If the major substrate for a patient's voiced complaint lies in the domain of emotional or social etiology (e.g., depression, anxiety, anger, secondary gain), then physical therapy, epidural steroid injections and low back pain will not effectively address the symptoms. Alternatively, if a patient's enduring pain is labeled as emotional, then the pain can go under-managed.

There are now a large number of population studies that demonstrate that diagnostic physician errors tend to underestimate and overestimate the psychosocial factors that impact patient's pain complaints. For example, 27% of all patients suffering from chronic arthritis suffer from major depression; many of these individuals go under treated for their depression. Similar figures exist for many other chronic musculoskeletal conditions. On the other hand, other studies find that the majority of patient's with chronic non-malignant pain do not receive adequate pain control from their treating physicians. Methodologies that properly identify and separate the pathophysiologic, emotional and social components of an individual's pain symptoms will help identify the appropriate approach to the subject's treatment. There will be more accurate diagnoses and better utilization of healthcare resources (with a reduction or cost and an improvement in outcome).

The co-morbidity of pain and emotional conditions has been established in almost every population study where it has been sought. For example, 27% of patients with arthritis suffer from identifiable depressive disorders and 35% had identifiable anxiety disorders. There has been a clear link established between fibromyalgia and psychiatric disorders. Similar juxtapositions have been found in failed low back syndrome, neuropathic pain syndromes such as diabetic neuropathy, and others.

One relevant question is that of etiology: whether the emotional disorder is caused by or causative of the pain complaint. Population studies suggest that both situations can arise. There are certainly cases where the family and personal history of depressive and anxiety syndromes pre-existed the development of pain complaints. Alternatively, there are certainly circumstances where there has been no antecedent psychological history prior to an identifiable pain syndrome and the subsequent development of a psychiatric disorder. There are three major divisions of emotional disorders that will be separated here for nosologic and analytic purposes.

These include psychotic disorders, depressive disorders, and anxiety disorders. They are not mutually exclusive and may co-exist. Frank psychosis can co-exist with pain syndromes. Fortunately, this is a relatively rare combination and will not be discussed further. As mentioned above, anxiety disorders and pain syndromes can be co-morbid. The anxiety syndrome may be generalized and have no causative relationship to the specific pain syndrome, (e.g., a patient with a generalized anxiety disorder may get into a car accident and then suffer symptom magnification as a manifestation of the underlying psychiatric syndrome). The anxiety syndrome might be based on pre-existing phobias and fears that are situationally specific (e.g., a patient with prior shoulder problems might become excessively anxious about a new knee injury). In both these cases, the anxiety syndrome has a primary causative relationship to the experienced pain symptom. Alternatively, an individual with a painful back injury may become anxious because his job security is threatened; this would be an example of a generalized anxiety secondary to the pain syndrome. Similar examples can be evoked regarding the co-existence of a depressive disorder and a pain syndrome. It also should be noted that anxiety/depression disorders can occur together. Some patients will have both.

The above brief outline demonstrates that the clinician faces a difficult conundrum when confronted with a chronic pain patient (where these interactive problems may or may not be manifest). Methodologies that rationally and clearly identify those individuals with significant emotional components to their pain complex would again improve diagnostic accuracy and management. As previously mentioned, 25% of all individuals with low back injuries fail to return to work within one month of injury. These individuals account for 75% of all costs associated with the management of low back problems. Large population studies document that there is a poor correlation between the severity of the injury, the pain complaints, radiological findings, and the outcome. Experience suggests that up to one-half of all these "treatment failures" may be due to improperly diagnosed and managed emotional factors.

Two of the social ills that taint the discipline of pain management are substance abuse and malingering. Substance abuse can be subdivided into two categories: social abuse and addiction. Addiction has a specific diagnosis as "a primary, chronic neurobiological disease, with genetic, psychosocial and environmental factors influencing its development and manifestations." It is characterized by behaviors that include one or more of the following: impaired control over drug use, compulsive use, continued use despite harm, and craving." Drug abuse, on the other hand, is characterized by "the conscious, often psychosocially motivated use of illicit substances and medications outside the scope of usual medical practice, but with the ability to stop drug use when harmed."

Allied with these are the issues of drug diversion for sale and distribution. This problem is again epidemic in our nation. In 2002, estimates suggested that 30 million Americans used prescription pain medications for non-medical purposes. In the same year, 1.5 million Americans (i.e., 0.5% of the population) abused or depended on prescription pain medications for non-medical reasons. Extrapolating from this data, one can estimate that there is a substantial risk that substance abusers or addicts or others will present routinely to physicians complaining of chronic pain. This problem will be even more complex when such individuals have identifiable anatomic entities that are often correlated with but are not inevitably associated with pain syndromes (e.g., herniated spinal discs, arthritic bony changes, fibromyalgia). Some studies suggest that up to 10% of all patients with chronic pain syndromes demonstrate aberrant behaviors reflective of possible drug abuse. Some of this may be due to unmanaged pain, emotional domain issues or social issues. A key challenge for the future will be the accurate assessment of this population of individuals.

Another social ill of our society is malingering for secondary gain. Malingering is the feigning of disability or symptoms in the effort to avoid one's duty or to obtain secondary compensation. It covers a wide spectrum of misbehavior from complete fabrication (i.e., faking an injury) to partial symptom magnification of a known and reproducible injury. It must be distinguished from the emotional disorders discussed above (these can also be feigned)

and true psychiatric disorders (i.e., factitious disorders commonly known as Munchausen's syndrome or Munchausen's by proxy). The prevalence of malingering in our society is unknown. It is higher in cases of pending litigation and indemnity. Significant malingering elements may be present in approximately 5% of all workers' compensation cases. Patient fraud is rampant in Social Security, Medicare and Medicaid. There is an estimated $1.6 billion dollars of Medicaid fraud perpetrated in Florida each year. Again, methodologies that objectively identify the existence of socially mediated pain complaints will reduce healthcare and indemnity costs in our nation.

A final correlate of the emotional and social domains of pain management is the domain of motivation. It is related but not completely dependent of the other aspects of pain complaints. Individuals can suffer pathophysiologic pain complaints and/or emotive pain complaints; these patients however may or may not be motivated to improve. For example, a patient with a chronic low back pain and no emotional overlay may still not be motivated to rehabilitate. Conversely, a patient with a severe generalized anxiety disorder may truly wish to improve through medications and counseling. As an aside, socially-mediated pain complaints do not require motivation for improvement of their pain symptoms, because by definition the pain symptoms are largely feigned; the key then is identification. The old adage states "where there is a will, there is a way." Conversely, one might state "where there is no will, there is no way." Once the major domains underlying a subject's pain symptoms can be identified, then secondary testing can elucidate whether or not there are issues with motivation.

Although population studies have clearly identified the scope of the problem in the assessment of chronic pain, applying these findings to the individual patient has not been successful. The complexities of the problem and the limitations of the "bedside" evaluation have resulted in significant diagnostic uncertainty and error.

The current medical paradigm for the assessment of an individual presenting with pain symptomotology is quite imprecise. After a clinical history, the physician attempts to verify the pathophysiologic pain by a clinical examination. The physician examines the patient by using an acceptable "painful stimulus" while monitoring mostly the patient's verbal response and associated body reactions. The stimulus is usually an unmeasured physical input such as palpatory pressure, active or passive range of motion, or a sensory stimulus (such as rubbing or a pin prick). The patient's monitored response is usually verbal (e.g., "That hurts") but may be associated with other physical manifestations such as wincing, withdrawal, or others. There are several limitations to this paradigm; these will be treated separately.

One limitation is the ambiguity of the patient response. The physician is currently largely dependent on the patient's response to the ungraded stimulus. In cases of substance abuse, addiction, medication diversion, social secondary gain, malingering, and factitious disorder, the patient can feign or exaggerate the response to mislead the physician into an improper assessment as to diagnosis or severity of the condition. This will lead to over-prescribing of medications, diagnostic tests or other treatment. It can lead to unfair compensation or assignment of social disability.

Further, in patients with emotional disorders, the pain symptoms may be tainted by an unconscious exaggeration of the stimulus and or its consequences. Patients with anxiety will tend to exaggerate the pathophysiologic intensity of the problem (e.g., the person who is afraid of the dentist will jump when the dentist touches the teeth; this does not mean that the tooth itself is biologically tenderer. A depressed patient may see the world in more plaintive and melancholic overtones so that everything "hurts more." This then can lead to inaccurate assessment of the underlying biologic component of the pain. Conversely, the patient with under treated pain may have a secondary anxious and depressive presentation that leads the doctor to conclude that the problem is primarily psychological.

Another limitation is the incomplete assessment of the patient response. As delineated in the definition of pain, the pain response has other components to its biological profile. These include the autonomic and physiologic responses that go largely unmonitored by the bedside physician. They include changes in vascular responsiveness (e.g., pulse rate, blood pressure, and peripheral vascular tone), skin resistance (due to sweating and other responses as measured by Galvanic changes), and overall muscle tone (e.g., anticipatory and reactive muscle tensing). These responses are extremely reproducible and follow very well known biologic principles and mechanisms. By routinely assessing the complex pain patient with these additional measures, the physician will be better able to grade the pain response and its components. This will be discussed more completely below. These well known observations will allow an expanded and more precise delineation of the individual's voiced pain experience.

Further, the physician must rely on his observational experience and acumen to assess all factors concerning the pain response. These include the severity of the response, the presence or absence of anticipatory (i.e., anxiety-related) phenomena, the presence or absence of post-stimulus emotive responses, and patient forthrightness. By monitoring and recording the autonomic and physiologic parameters just introduced, the physician will be better able to assess the three major domains of the patient pain profile.

Another limitation is the imprecision of the evocative stimulus. The clinician generally uses non-measured stimuli to create his observations. They are usually applied once and therefore do not guarantee reproducibility and accuracy. If the physician palpates the sore knee once, the patient complains and the physician infers. This leads to a great deal of imprecision in the inferences drawn. If a measured stimulus is applied repetitively in a systematic fashion and then combined with precise and comprehensive monitoring, then improved diagnostic accuracy will result.

The diagnostic uncertainty and error concerning the individual with pain complaints results in the current quagmire that confronts the medical community and society in general when dealing with this epidemic problem. The current quagmire that confronts the medical community and society in general when dealing with this epidemic problem.

Therefore, a need exists to overcome the problems with the prior art as discussed above, and particularly for a more efficient way of evaluating pain in humans.

SUMMARY OF THE INVENTION

Briefly, according to an embodiment of the present invention, a method for evaluating pain experienced by a human is disclosed. The method includes applying a first noxious stimulus to a normative site on the human, wherein the first noxious stimulus is applied below a pain threshold of the human and logging a first information associated with the first noxious stimulus. The method further includes applying a second noxious stimulus to a source of the pain in the human, wherein the second noxious stimulus is applied until pain threshold is reached and logging a second information associated with the second noxious stimulus. The method further includes increasing the second noxious stimulus until pain tolerance is reached and logging a third information associated with the second noxious stimulus. The method further includes continuing to apply the second noxious stimulus until the human can no longer tolerate the second noxious stimulus and logging a fourth information associated with the second noxious stimulus.

In another embodiment of the present invention, a system for evaluating pain experienced by a human is disclosed. The system includes a measuring apparatus for measuring information associated with a first and second noxious stimulus applied to a human, wherein the first noxious stimulus is applied to a normative site on the human below a pain threshold of the human, the second noxious stimulus is applied to a source of the pain in the human until pain threshold is reached, the second noxious stimulus is applied until pain tolerance is reached and the second noxious stimulus is applied until the human can no longer tolerate the noxious stimulus. The system further includes a data storage device for storing a first information from the measuring apparatus when the first noxious stimulus is applied below a pain threshold, storing a second information from the measuring apparatus when the second noxious stimulus is applied at pain threshold, storing a third information from the measuring apparatus when the second noxious stimulus is applied at pain tolerance, and storing a fourth information from the measuring apparatus when the human can no longer tolerate the second noxious stimulus.

In another embodiment of the present invention, an information processing system for evaluating pain experienced by a human is disclosed. The information processing system includes a receiver for receiving a first information from a measuring apparatus for measuring information associated with a first and second noxious stimulus applied to a human, wherein the first noxious stimulus is applied to a normative site on the human below a pain threshold of the human, receiving a second information from the measuring apparatus when the second noxious stimulus is applied to a source of the pain in the human at pain threshold, receiving a third information from the measuring apparatus when the second noxious stimulus is applied at pain tolerance, and receiving a fourth information from the measuring apparatus when the human can no longer tolerate the second noxious stimulus. The information processing system further includes a data storage device for storing the first information, the second information, the third information and the fourth information. The information processing system further includes a processor configured for determining whether the pain experienced by the human originates from biological, social or psychological factors, based on the first information, the second information, the third information and the fourth information.

The foregoing and other features and advantages of the present invention will be apparent from the following more particular description of the preferred embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings. Additionally, the left-most digit of a reference number identifies the drawing in which the reference number first appears.

FIG. 5 is an exemplary chart that can be used to log information garnered from measurement apparatus, in one embodiment of the present invention.

DETAILED DESCRIPTION

Figure 1:
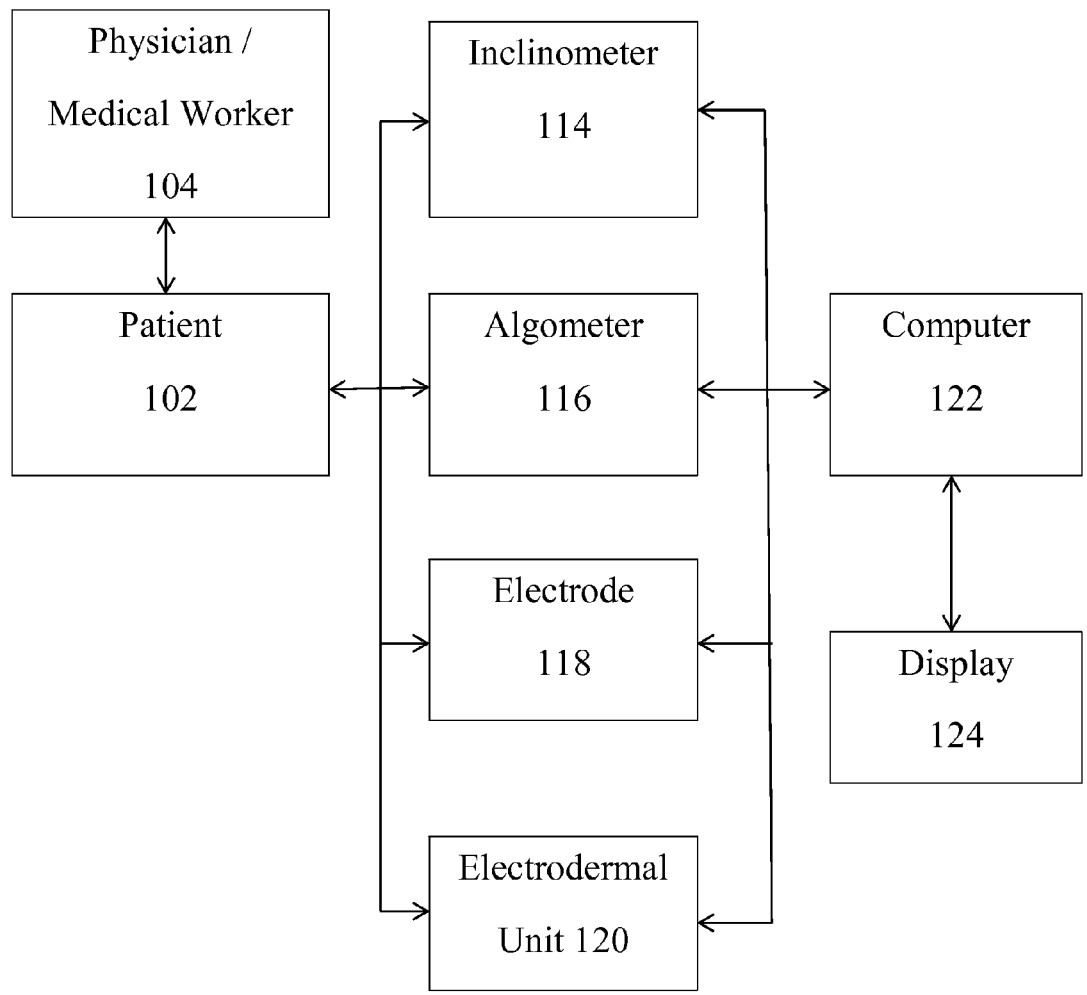
FIG. 1 is a block diagram generally showing the elements that are utilized to perform one embodiment of the present invention.

According to an embodiment of the present invention, a method for evaluating the human pain experience is disclosed. The method combines at lest five elements: (1) a pre-test history and physical exam (2) the precise application of quantifiable sensory stimuli (pressure stimuli, active or passive range of motion stimuli, or the cutaneous sensory stimuli in the form of electrical current) to the patient; (3) the application of these stimuli to specific patient-controlled levels of response (i.e., pain threshold, or pain tolerance levels as defined by the IASP); (4) the simultaneous recording of the patient's verbal response and non-verbal body reactions: and (5) the use of the patient as his or her own control by comparing the "baseline/normative" response taken at an asymptomatic site versus the specific "painful/test" site. One embodiment of the present invention (a) precisely monitors in individuals the temporal and quantifiable relationships of sensory stimuli with simultaneous verbal and non-verbal patient responses at internationally recognized pain stimulus levels; and (b) compares this precision data from body site to body site. This accuracy yields information about an individual's pain experience and its components.

With regard to the history and physical exam, a specific history and physical data base allows for the standardization of diagnoses, electrode placements, and the various historical elements that may influence the testing procedure. By combining this history and physical information with test results (specifically on the baseline/normative data), a database on the variations in human pain experience with gender, age, cultural and sociologic influence can be created. This database can be used in the elaboration of more accurate and statistical typing of a new patient's response for more complete and particular diagnoses.

With regard to recording techniques, recording electrodes can be applied to the test subject in specified locations to maximize information yield. Surface electromyographic activity can be measured at four sites. Two sites are general and monitor the subject's overall muscle tension in response to the physical stressor. Two sites are stimulus specific (i.e., close to the applied stimulus) to evaluate elements of voluntary or involuntary guarding that are site specific (i.e., anxiety or feigned responses). Autonomically-mediated galvanic skin responses can be measured in the form of skin conductance responses and skin conductance latencies. Autonomically-mediated vasomotor responses can be monitored in the form of heart rate, skin temperature, and pulse height (using plethysmography). These measures are continuously monitored during a definite test stimulation protocol to analyze the temporal and quantitative changes from baseline in response to the exactly applied stimulation.

With regard to stimulation techniques, exact sensory stimuli can be first applied to a normative, "pain-free" site to pre-defined, internationally recognized levels (see below for detailed explanation). Any one of four sensory stimuli can be applied: (1) pressure-using standardized algometry equipment, precise palpation pressure can be applied to a particular body site; (2) passive range of motion-using an inclinometer, a precise passive or active range of motion can be measured to a specific articulation. (3) sensory stimulus-using a biometric electrical signal generator, a precise superficial sensory stimulus can be applied; and (4) active resistance-using a pressure gage, the amount of force required to induce a level of pain experience (be that threshold or tolerance levels) can be assessed. The choice of stimulation technique will be dependent on the patient's presentation and diagnosed pain syndrome. Multiple different stimuli and sites can be evaluated in a single individual dependent on the clinical picture. The history and physical examination form the foundation for the protocol determination.

With regard to the use of international standards and a specific protocol, most pain evaluations use only the patient's evaluation of the overall experience in a unimodal intensity scale (e.g., a visual analog scale of the pain experience severity). One embodiment of the present invention uses IASP defined levels of the pain experience (specifically, pain threshold and pain tolerance levels). These levels are less variable and avoid some of the inherent ambiguities of the linear pain scales. The protocols also repeat each stimulus three times at a given site and then take an average. This allows for the assessment of consistency and inconsistency of the response according to known statistical values of variance. The use of a specific temporal protocol allows accurate determinations regarding anticipatory responses, post-response exaggeration, and other temporal relations between the pain stimuli and the verbal/nonverbal responses.

One embodiment of the present invention allows the patient to be their own control. The sensory stimulus is first applied to a normative, non-painful body site. This first site data sets a patient-specific baseline that can then be compared to responses in painful test sites. The use of a patient specific control site mitigates multiple potential factors such as gender, age, medications, race, and others. It simplifies the initial statistical analysis. It also duplicates bedside clinical paradigms whereby physicians often compare patient responses from one body region to another.

The present invention provides an algorithm for the assessment of an individual subject's pain symptoms. The algorithm juxtaposes measured evocative stimuli, the patient's voiced pain response, and measurable autonomic and physiologic responses. These assessments are performed according to protocols to maximize reproducibility and diagnostic precision. The algorithm allows the clinician reader to objectively, accurately, and impartially assess the underlying components of the pain complaints in terms of its pathophysiologic, emotional and social domains. The present invention comprises three test components: the voiced pain response, the measurable autonomic and physiologic responses, and the measured evocative stimuli.

With regards to the patient's voiced pain response, the IASP defines two different types of standard patient subjective pain complaints; specifically, the pain threshold and the pain tolerance level. The algorithm of the present invention identifies a third patient subjective complaint—the endurance for pain tolerance. A pain threshold (PTh) is the least experience of pain which a subject can recognize. A pain tolerance level (PToL) is the greatest level of pain which a subject is prepared to tolerate. The endurance of pain tolerance (EPT) is the length of time a subject is prepared to endure the PToL.

The IASP emphasizes that each of these levels document the totality of the patient's personal subjective experience. They are determined by a mixture of the pathophysiologic domain and emotional domain as defined previously. The IASP does not specifically discuss the social domain that taints many clinical assessments. These established definitions are useful in establishing standard degrees for the patient's verbal response. PTh instructions may be: "Indicate when the stimulus intensity first begins to feel 'painful.'" PToL instructions may be: "Tell me when the intensity becomes unbearable." EPT instructions may be: "Tell me when to stop." Each of these levels is reasonably reproducible and identifiable. The instructions form the basis on which other aspects of the algorithm can be accurately measured. In each embodiment of the present invention, one of these verifiable subjective pain report levels will provide the basis of the overall evaluation.

The term "noxious stimulus" applies to the level of stimulation that threatens or causes tissue damage. It is often confused with the above subjective experiences but it is actually very different. Consider the patient under general anesthesia, a researcher could still accurately establish the level of a noxious stimulus (i.e., heat stimulation causes a tissue to injure); the subjective experience and levels would not apply.

With regards to the measurable autonomic and physiologic responses, when the body is subject to a new physical or emotional stressor, there is inevitably a response. This has been called "the fight or flight response." It is largely involuntary and mostly mediated by the autonomic (parasympathetic and sympathetic) system. There is also a largely involuntary muscle tension response that is more directly mediated by the somatic nervous system. Over a short time epoch (seconds to minutes), the response will persist as long as the stressful stimulus continues. These autonomic and muscle tension responses are ubiquitous in humans. They form the basis for biofeedback relaxation training and have been applied therapeutically in medico-psychological fields for several decades. There are myriad of such reactions like the vascular responses (pulse rate, blood pressure, pulse height and others), galvanic skin responses (skin conductance response, skin conductance latency), surface electromyography (EMG) recordings, pupillary responses, piloerection reactions and others.

Despite decades of utilization of autonomic physiology in therapeutic venues, this physiology has not been applied to the diagnostic side of medicine. In the present invention, this physiology's application to the evaluation of pain symptoms leads to a paradigm shift and resolves the limitations of the previously described response ambiguities. Because the autonomic and somatic neurologic system reacts to perceived (i.e., emotional) stressors as well as to actual physical stimulation, careful monitoring autonomic and EMG reactivity allows the observer to unequivocally identify the emotional domain associated with the pain experience. For example, one can apply these principles to the pain threshold stimuli. When pain threshold amounts of stimuli are applied, pre-stimulation increases in autonomic and EMG activity reflect anticipatory depression or anxiety-related phenomena. Post-stimulation increments these parameters indicate pain-related anxiety or depressive responses that augment the patient's pain reaction.

With regards to the measured "painful" stimulation technique, the innovative and original testing paradigm utilizes graded measurable stimuli for four major clinical stimuli-palpatory pressure (known as algometry or dolorimetry), range of motion (called goniometry or inclinometry), topical sensory stimulation (e.g., an electrical current), and force resistance. Each of these inputs is selective for different pathophysiologic phenomena. Palpation is often applied for myofascial type pain syndromes (such as fibromyalgia). Range of motion is helpful in articular pain syndromes. Electrical current can be very useful in many neuropathic pain syndromes, especially those characterized by hyperesthesia, allodynia, and hyperpathia. Finally, force-related pain can be valuable in any of the above, and as a graded measure of the motivational aspects associated with pain syndromes. Each of these stimulation techniques can be applied in a quantified and reproducible fashion to maximize diagnostic information. In an embodiment of the present invention, each of these stimuli is specifically chosen to match the individual subject's pain syndrome.

With regards to the integration of the diagnostic components in a diagnostic algorithm, the embodiment of the present invention integrates all three testing features into patient specific testing algorithms. The present invention combines the patient's subjective pain response with a precise measured stimulus and a comprehensively monitored physiologic response profile. Each patient subject acts as his own control. One critical aspect of the test paradigm is that the chosen painful stimulus is first applied to a non-painful "normative" test site. The choice of the neutral site allows the testing algorithm to create a patient-specific "pain experience" baseline. Thus, this step therefore mitigates consideration of many pre-existing substrates of an individual's pain experience (genetics, cultural heritage, and many learned behaviors). These chronic features have often been evinced as grounds to confound the correct assessment of the patient's pain symptomotology. After obtaining the baseline response, attention is then directed to the patient's painful body region. The stimulation is then repeated in the same fashion. This changes in stimulus intensity to reach a given verbalized pain level (be it PTh, PToL, and EPT) can be documented. Different autonomic and physiologic response levels and profiles can be documented.

FIG. 1 is a block diagram generally showing the elements that are utilized to perform one embodiment of the present invention. FIG. 1 shows the patient 102 and the physician or medical worker 104 evaluating the patient 102. The physician applies various stimuli to the patient 102 during the evaluation process. The noxious stimuli applied to the patient can include moving a portion of the human, moving a limb of the human about a joint, applying pressure to a portion of the human, applying an electrical pulse to a portion of the human; and allowing the human to push or pull with force using a portion of the human. Also shown are various apparatus used to measure the stimuli applied to the patient 102.

There are multiple commercially available devices that measure clinical stimuli used to supplement the clinician's bedside evaluation. These devices can measure and apply pressure (called algometry or dolorimetry) and measure range of motion (called goniometry or inclinometry). Further, there are devices that can provide graded "painful" sensory stimuli (usually safe amounts of electrical current).

Equipment, such as a vasomotor or electrodermal apparatus 120, can be used to monitor autonomic physiologic functions including pulse rate, blood pressure, skin temperature, skin conductance level, and skin conductance response.

The apparatus 120 also can measure surface electromyography (EMG) activity at two locations. An inclinometer 114 (or goniometer) measures the incline or degree of motion of a limb or portion of the patient 102, an algometer 116 measures the amount of pressure applied to the patient 102 and an electrode 118 measures the amount of electricity applied to the patient. Thus, the present invention can accurately monitor the existence and magnitude of various physiologic responses of involuntary and voluntary type. This capability allows more precise characterization of the subject's pain experience as discussed below.

FIG. 1 also shows a computer 122 for analyzing the measurement data garnered from the measuring equipment 114, 116, 118, 120 and determining whether the pain experienced by the human originates from biological, social or psychological factors, based on the information garnered. Also shown is a computer display 124 for displaying these results.

In an embodiment of the present invention, the computer system of computer 122 is one or more Personal Computers (PCs) (e.g., IBM or compatible PC workstations running the Microsoft Windows operating system, Macintosh computers running the Mac OS operating system, or equivalent), Personal Digital Assistants (PDAs), hand held computers, palm top computers, smart phones, game consoles or any other information processing devices. In another embodiment, the computer system of computer 122 is a server system (e.g., SUN Ultra workstations running the SunOS operating system or IBM RS/6000 workstations and servers running the AIX operating system). An example of a computer 122 is explained in greater detail below with reference to FIG. 4.

In an embodiment of the present invention, the computer 122 is connected to a circuit switched network, such as the Public Service Telephone Network (PSTN). In another embodiment, the network is a packet switched network. The packet switched network is a wide area network (WAN), such as the global Internet, a private WAN, a local area network (LAN), a telecommunications network or any combination of the above-mentioned networks. In yet another embodiment, the network is a wired network, a wireless network, a broadcast network or a point-to-point network.

The present invention measures pain thresholds using, for example, pressure, tissue stretch, and electrical noxious stimuli. The present invention first tests non-injured, asymptomatic areas, then tests the specific regions of disabling pain complaints, and finally compares the responses. The test results therefore first establish the subject's nonspecific pain threshold and pain tolerance levels. The present invention mitigates the role of the individual's nonspecific psychosocial background. This allows the clinician to focus on the specific psychobiological components underlying the specific disabling pain complaints. A few examples below elaborate this point.

In a first example, an individual's general state of anxiety or depression will modify the pain threshold for all body regions and not specific to the injured area. Take the case of a patient with a pre-existing major depression and a newer chronic low back pain. The patient may complain significantly of the low back pain with clinical findings of restricted flexion and tender palpation (via the well-known psychological mechanism of somatization). The results garnered from the present invention show similar pain thresholds, tolerance levels, and autonomic responses in the non-injured and low back regions. Thus, the psychobiologic responses in both regions are similar to the putative noxious stimuli. The conclusions are: (a) the low back tissues are not seriously dysfunctional; (b) the patient does not have a secondary anxiety due to severe localized tissue pain; (c) the underlying cause of the pain experience is psychiatric in origin.

In a second example, a patient's adjustment disorder will modify results specific to the injured regions. A patient with a low back injury develops unremitting pain with a secondary adjustment anxiety disorder. The results garnered from the present invention show that autonomic responses occur early during stimulus initiation, even before the patient voices pain commencement. The local pain threshold and tolerance is approximately the same or mildly reduced, but the voiced complaints and the autonomic responses are magnified. The anticipatory and augmented autonomic changes create inescapable inferences: (a) the subject anticipates and magnifies the noxious stimulus on a psychobiological level; and (b) the subject's tissues are not overtly tender from the noxious stimulus per se.

In a third example, a patient with chronic pain may have biologically damaged tissue unidentified by current diagnostic testing. A patient complains of intermittent but persistent low back pain radiating down the right leg for two months after a slip-and-fall injury. A Magnetic Resonance Image (MRI) of the back is fairly unremarkable except for mild, commonly seen arthritic changes. An EMG/nerve conduction study (NCS) shows mild chronic denervation in the right L5/S1 myotomes. Clinical exam shows guarding behavior, limping with positive straight leg raising but a normal neurologic examination. The results garnered from the present invention show that there are autonomic changes without anticipation, decreased pain threshold and tolerance levels upon right (but not left) straight leg raising and electrical noxious stimuli. The inferences are that the patient has a significant peripheral neurogenic pain syndrome despite unremarkable diagnostic testing.

The present invention includes clinical modules for exercising the method of the present invention for the major subtypes of conditions that are anticipated. Modules exist for each of the following conditions: (a) general post-traumatic complaints; (b) myofascial traumatic and non-traumatic conditions; (c) arthritic traumatic and non-traumatic conditions; (d) neuropathic traumatic and non-traumatic conditions and (e) voluntary or involuntary muscle guarding. By using separate modules, there is flexibility in meeting almost all clinical situations presented.

The present invention further includes four major testing protocols to match each of the major clinical modules. From a teleologic perspective, the body is most concerned with the resultant biologic nature of the injuries, i.e., multiple non-specific traumatic mechanisms, predominantly arthritic (focal or multi-focal), predominantly myofascial, etc. The testing protocols are moved from site-to-site and format-to-format as required by the clinical specificity and diversity. Each testing protocol is comprised of one or more of five basic testing paradigms: 1) joint pain (more precisely, range of motion noxious response), 2) myofascial pain (more precisely, palpatory pressure noxious response), 3) neuropathic pain (electrical stimulation response), 4) force output noxious stimuli, and 5) muscle guarding protocols.

Figure 2:
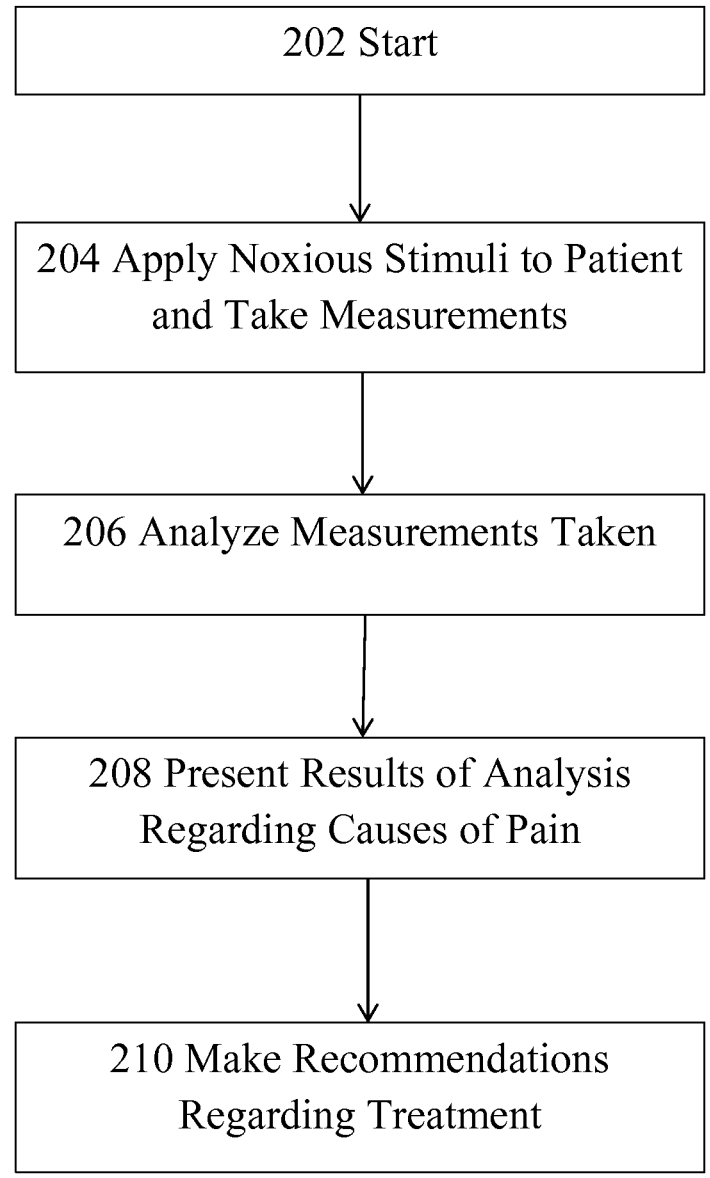
FIG. 2 is a flowchart showing the overall control flow of one embodiment of the present invention.

FIG. 2 is a flowchart showing the overall control flow of one embodiment of the present invention. The control flow of FIG. 2 begins with step 202 and moves immediately to step 204. In step 204, noxious stimuli are applied to the patient 102 by the physician 104 and the measurements are taken. This step is discussed in greater detail with reference to FIG. 3 below. In step 206, the measurement data garnered from the measuring equipment 114, 116, 118, 120 is analyzed (by, for example, a computer 122) and it is determined whether the pain experienced by the human originates from biological, social or psychological factors, based on the information garnered. In step 208, the results of the determination are presented to the patient 102, the physician 104 or both via, for example, a computer display 124 for displaying these results. In step 210, based on the results of step 208, the physician 104 makes recommendations to the patient 102 regarding treatment of the pain.

For the noxious stimulus types, pain threshold, pain tolerance, and maintenance of pain tolerance are measured. In an embodiment of the present invention, these measurements are performed according to the following: 1) initial baseline (approximately one minute), 2) stimulus to pain threshold (five seconds), 3) stimulus to pain tolerance (five seconds), 4) maintenance of pain tolerance (five seconds) and 5) rest period (lasting 30 seconds or more, if needed). Thus, a stimulation cycle will last approximately 45 seconds. During the first 10 seconds, there is a relatively quick ramp of increasing noxious stimulation with monitoring of the patient's voiced response (according to established principles). The epoch between 10 and 15 seconds, the patient is asked to maintain his tolerated painful experience. Then the patient rests with no stimulus. For each type of noxious stimulation and site, this cycle is repeated three times. The purpose of the repetition is establishing reproducibility and patient reliability. In one embodiment of the present invention, the patient hold a "clicker" device that is clicked to indicate when he or she achieves the three designated outcomes, i.e., pain threshold, pain tolerance and termination.

In another embodiment of the present invention, for each type of stimulation, the test protocol includes the selection of a normative, unaffected site on the patient's body followed by the test, affected site. For example, in an individual with right shoulder pain, the test protocol would first be performed on the normative, unaffected left shoulder to establish a patient-specific response normative baseline. The second part of the test repeats the same stimulations on the affected right shoulder to assess differences in autonomic and verbal response.

Range of motion stimuli is performed using a hand-held inclinometer 114. For hinge joints, there is only one plane of motion so the choice of direction is obvious. For rotational or multiple joint regions (i.e., shoulders, hips and spine), the clinician/technician can use two planes of motion that are most applicable to a patient's specific joint/range of motion complaint. Algometry is performed using a hand held algometer 116 that can be connected to a computer 122. Electrical stimulation is performed using an electrode 118 that can also be connected to a computer 122.

Force testing/joint compression stimulation is used to establish effort and establish non-specific internal compression forces. A hand held force gauge (such as an algometer) can be used and the patient is asked to contract their muscles in a given plane of motion (i.e., initiating active range of motion) isometrically. The force output is measured in comparison to the three outcomes of pain threshold, tolerance and termination.

Muscle guarding of an involuntary and voluntary type are very common in musculoskeletal pains. By reviewing EMG readings of the patient 102, the onset of muscle activity in response to passive range of motion or algometry stimuli can be assessed. The onset of this activity is compared with the onset of autonomic responses to assess whether the muscle activity precedes or follows our various monitored responses. This assessment is used to evaluate voluntary versus involuntary guarding.

Figure 3:
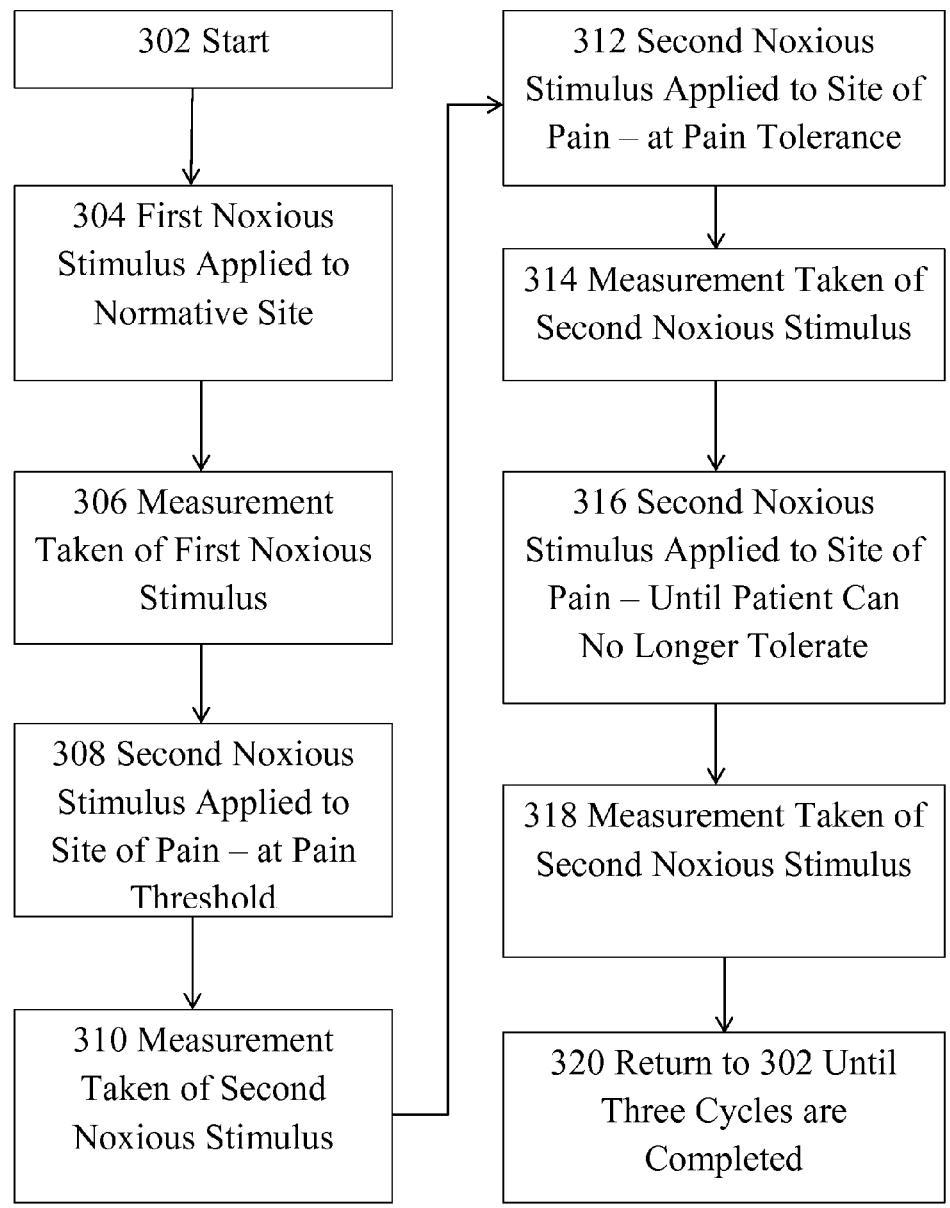
FIG. 3 is a flowchart showing the control flow of the data acquisition process of one embodiment of the present invention.

FIG. 3 is a flowchart showing the control flow of the data acquisition process of one embodiment of the present invention. The flow chart of FIG. 3 provides more detail on step 204 of FIG. 2. The control flow of FIG. 3 begins with step 302 and moves immediately to step 304. In step 304, a first noxious stimulus is applied to a normative site on the human, wherein the first noxious stimulus is applied below a pain threshold of the human. In step 306, a first information associated with the first noxious stimulus is recorded. In step 308, a second noxious stimulus is applied to a source of the pain in the human, wherein the second noxious stimulus is applied until pain threshold is reached.

In step 310, a second information associated with the second noxious stimulus is recorded. In step 312, the second noxious stimulus is increased until pain tolerance is reached. In step 314, a third information associated with the second noxious stimulus is recorded. In step 316, the second noxious stimulus continues to be applied until the human can no longer tolerate the second noxious stimulus. In step 318, a fourth information associated with the second noxious stimulus is recorded. In step 320, steps 302-318 are repeated once more until three cycles are completed.

In one embodiment of the present invention, the first information, the second information, the third information and the fourth information each comprise at least one of an angle of a portion or a limb of the human, an amount of pressure applied to a portion of the human, an amount of electricity applied to a portion of the human and an amount of pressure applied by a portion of the human. Therefore, the first information, the second information, the third information and the fourth information each comprise at least one of a degree or radian value, a first pounds-per-square-inch value, an amperage and/or voltage value and a second pounds-per-square-inch value.

FIG. 5 is an exemplary chart that can be used to log information garnered from measurement apparatus, in one embodiment of the present invention. The chart of FIG. 5 is used to log three trials of data automatically. Averages can be calculated, and standard deviation for inter-site comparisons can be figured. Also intra-trial trends can be seen for accommodation/anticipation and coefficients of variations for reliability. Subsequent use of other statistics (Student T-test, Chi-square's, etc.) can be applied to characterize the patient's autonomic response type, whether the inter-site variance is significant.

FIG. 5 includes four separate charts, 502, 504, 506 and 508. Each of the charts 502, 504 and 506 represent are used to input data from each of three trials conducted in accordance with the control flow of FIG. 3. The last chart 508 is used to average the data in the first three charts. Thus, the data entered into the cells of chart 508 are not directly from the readings taken but rather are averages that are garnered from the data in the first three trials, i.e., from the data in charts 502, 504, 506.

It is shown that each chart includes five rows for entering data. The first row in each chart, row 511, 521, 531 and 541 is used to enter data associated with the baseline reading. The second row in each chart, row 512, 522, 532 and 542 is used to enter data associated with the pain threshold reading. The third row in each chart, row 513, 523, 533 and 543 is used to enter data associated with the pain tolerance reading. The fourth row in each chart, row 514, 524, 534 and 544 is used to enter data associated with the pain termination reading. The fifth row in each chart, row 515, 525, 535 and 545 is used to enter data associated with a reading during a 25 second rest period.

It is further shown that each chart includes eight columns for entering data. The first column in each chart, column 551, is used to enter the amount of time associated with each of the pain threshold, pain tolerance and pain termination readings. The second column in each chart, column 552, is used to enter the angle associated with each of the pain threshold, pain tolerance and pain termination readings. The third column in each chart, column 553, is used to enter a first electromyography (EMG) reading associated with each of the baseline, pain threshold, pain tolerance, pain termination and rest readings. The fourth column in each chart, column 554, is used to enter a second EMG reading associated with each of the baseline, pain threshold, pain tolerance, pain termination and rest readings. It should be noted that the data entered into the cells of chart 508 are not directly from the readings taken but rather are averages that are garnered from the data in the first three trials, i.e., from the data in charts 502, 504, 506.

The fifth column in each chart, column 555, is used to enter a skin conductive response (SCR) reading associated with each of the baseline, pain threshold, pain tolerance, pain termination and rest readings. The sixth column in each chart, column 556, is used to enter a skin conductive latency (SCL) reading associated with each of the baseline, pain threshold, pain tolerance, pain termination and rest readings. The seventh column in each chart, column 557, is used to enter a pulse reading associated with each of the baseline, pain threshold, pain tolerance, pain termination and rest readings. The eighth column in each chart, column 558, is used to enter a pulse pressure reading associated with each of the baseline, pain threshold, pain tolerance, pain termination and rest readings.

Various aspects of the present invention, such as the determination process of step 206 of FIG. 2, can be realized in hardware, software, or a combination of hardware and software. A system according to a preferred embodiment of the present invention, such as the system of FIG. 1, can be realized in a centralized fashion in one computer system, or in a distributed fashion where different elements are spread across several interconnected computer systems. Any kind of computer system—or other apparatus adapted for carrying out the methods described herein—is suited. A typical combination of hardware and software could be a general-purpose computer system with a computer program that, when being loaded and executed, controls the computer system such that it carries out the methods described herein.

Various aspects of an embodiment of the present invention can also be embedded in a computer program product, which comprises all the features enabling the implementation of the methods described herein, and which—when loaded in a computer system—is able to carry out these methods. Computer program means or computer program in the present context mean any expression, in any language, code or notation, of a set of instructions intended to cause a system having an information processing capability to perform a particular function either directly or after either or both of the following: a) conversion to another language, code or, notation; and b) reproduction in a different material form.

A computer system may include, inter alia, one or more computers and at least a computer readable medium, allowing a computer system, to read data, instructions, messages or message packets, and other computer readable information from the computer readable medium. The computer readable medium may include non-volatile memory, such as ROM, Flash memory, Disk drive memory, CD-ROM, and other permanent storage. Additionally, a computer readable medium may include, for example, volatile storage such as RAM, buffers, cache memory, and network circuits. Furthermore, the computer readable medium may comprise computer readable information in a transitory state medium such as a network link and/or a network interface, including a wired network or a wireless network, that allow a computer system to read such computer readable information.

Figure 4:
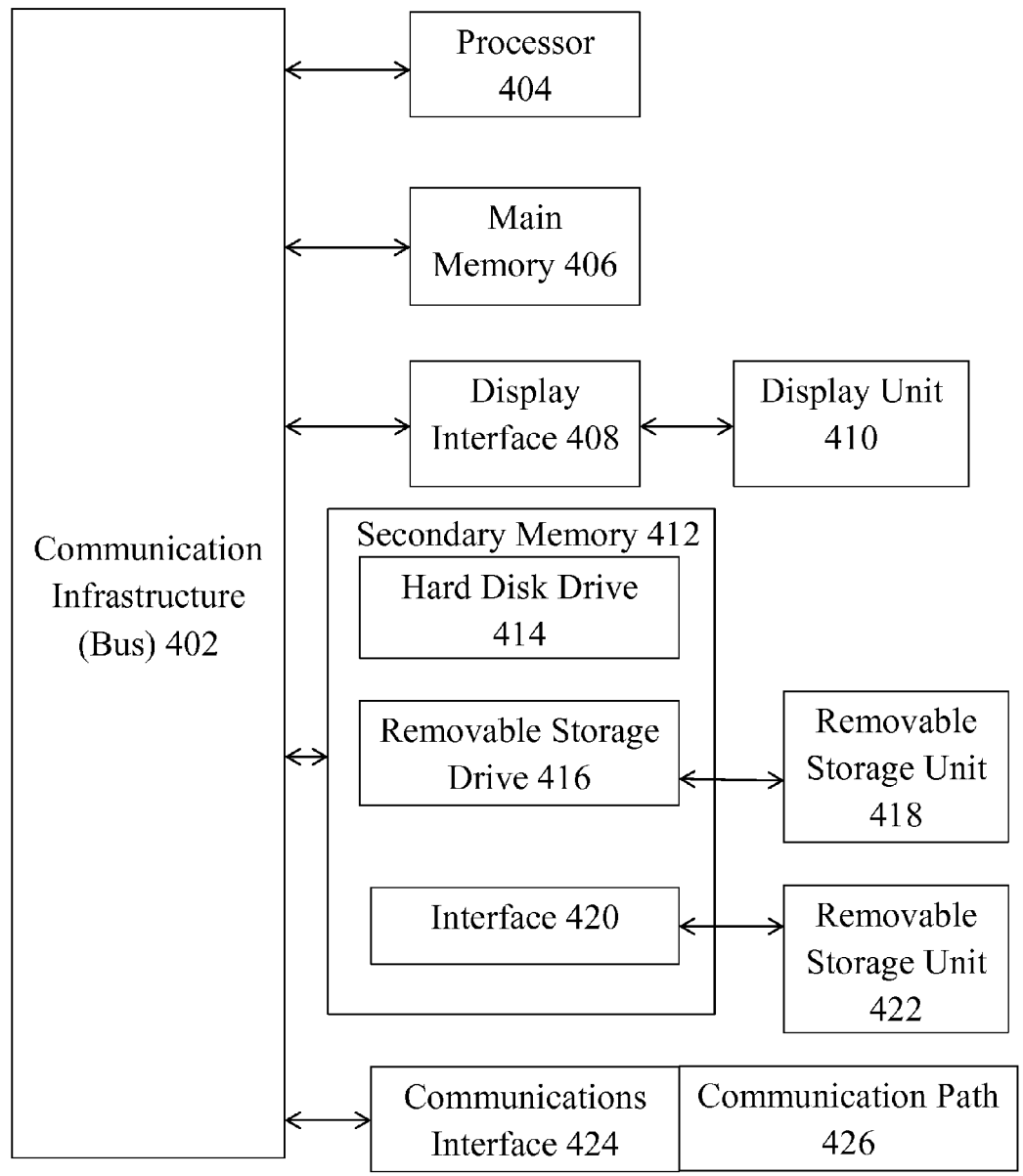
FIG. 4 is an information processing system useful for implementing one embodiment of the present invention.

FIG. 4 is a high level block diagram showing an information processing system useful for implementing one embodiment of the present invention. The computer system includes one or more processors, such as processor 404. The processor 404 is connected to a communication infrastructure 402 (e.g., a communications bus, cross-over bar, or network). Various software embodiments are described in terms of this exemplary computer system. After reading this description, it will become apparent to a person of ordinary skill in the relevant art(s) how to implement the invention using other computer systems and/or computer architectures.

The computer system can include a display interface 408 that forwards graphics, text, and other data from the communication infrastructure 402 (or from a frame buffer not shown) for display on the display unit 410. The computer system also includes a main memory 406, preferably random access memory (RAM), and may also include a secondary memory 412. The secondary memory 412 may include, for example, a hard disk drive 414 and/or a removable storage drive 416, representing a floppy disk drive, a magnetic tape drive, an optical disk drive, etc. The removable storage drive 416 reads from and/or writes to a removable storage unit 418 in a manner well known to those having ordinary skill in the art. Removable storage unit 418, represents a floppy disk, a compact disc, magnetic tape, optical disk, etc. which is read by and written to by removable storage drive 416. As will be appreciated, the removable storage unit 418 includes a computer readable medium having stored therein computer software and/or data.

In alternative embodiments, the secondary memory 412 may include other similar means for allowing computer programs or other instructions to be loaded into the computer system. Such means may include, for example, a removable storage unit 422 and an interface 420. Examples of such may include a program cartridge and cartridge interface (such as that found in video game devices), a removable memory chip (such as an EPROM, or PROM) and associated socket, and other removable storage units 422 and interfaces 420 which allow software and data to be transferred from the removable storage unit 422 to the computer system.

The computer system may also include a communications interface 424. Communications interface 424 allows software and data to be transferred between the computer system and external devices. Examples of communications interface 424 may include a modem, a network interface (such as an Ethernet card), a communications port, a PCM-CIA slot and card, etc. Software and data transferred via communications interface 424 are in the form of signals which may be, for example, electronic, electromagnetic, optical, or other signals capable of being received by communications interface 424. These signals are provided to communications interface 424 via a communications path (i.e., channel) 426. This channel 426 carries signals and may be implemented using wire or cable, fiber optics, a phone line, a cellular phone link, an RF link, and/or other communications channels.

In this document, the terms "computer program medium," "computer usable medium," and "computer readable medium" are used to generally refer to media such as main memory 406 and secondary memory 412, removable storage drive 416, a hard disk installed in hard disk drive 414, and signals. These computer program products are means for providing software to the computer system. The computer readable medium allows the computer system to read data, instructions, messages or message packets, and other computer readable information from the computer readable medium.

Computer programs (also called computer control logic) are stored in main memory 406 and/or secondary memory 412. Computer programs may also be received via communications interface 424. Such computer programs, when executed, enable the computer system to perform the features of the present invention as discussed herein. In particular, the computer programs, when executed, enable the processor 404 to perform the features of the computer system. Accordingly, such computer programs represent controllers of the computer system.

What has been shown and discussed is a highly-simplified depiction of a programmable computer apparatus. Those skilled in the art will appreciate that other low-level components and connections are required in any practical application of a computer apparatus.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

What is claimed is:

1. A method for evaluating pain experienced by a human, the method comprising the steps of: applying a first noxious stimulus to a normative site on the human, said noxious stimulus applied to the human includes moving a portion of the human in a manner to observe range of motion measured to a specific articulation, moving a limb of the human about a joint, or instructing the human to push or pull with force using a portion of the human, said force imparted by the push or pull resulting in a stimulus for evaluation, wherein the first noxious stimulus is performed below a pain threshold of the human;

continuously logging on a computer a first information associated with the first noxious stimulus before during and after the first noxious stimulus;

applying a second noxious stimulus to a source of the pain in the human, wherein the second noxious stimulus is applied until pain threshold is reached;

continuously logging on the computer a second information associated with the second noxious stimulus before during and after the second noxious stimulus;

increasing the second noxious stimulus until pain tolerance is reached;

continuously logging on the computer a third information associated with the second noxious stimulus before during and after the first noxious stimulus;

continuing to apply the second noxious stimulus until the human is no longer able to tolerate the second noxious stimulus; and continuously logging on the computer a fourth information associated with the second noxious stimulus before during and after the second noxious stimulus, each of said noxious stimulus is performed in time patterns including:

an initial baseline of approximately one minute;

a stimulus to pain threshold held for approximately five seconds;

a stimulus to pain tolerance held for approximately five seconds;

maintenance of pain tolerance held for approximately five seconds;

a rest period of thirty seconds or more;

the computer assesses the consistency and inconsistency of the response according to statistical values of variance by averaging each of the first, second, third, and fourth information to an average information record based on the repetition of each individual stimulus;

wherein said average record is used by a health care provider to determine the origination of pain from at least one of biological, social, or psychological factors, and wherein the logged information is evaluated to identify an emotional domain associated with pain experience.

2. The method of claim 1, further comprising: withdrawing the second noxious stimulus; and executing all previous steps.

3. The method of claim 2, further comprising: determining whether the pain experienced by the human originates from biological, social or psychological factors, based on the first information, the second information, the third information and the fourth information.

4. The method of claim 1, wherein the first step of performing a first manipulation comprises: performing a first manipulation being a first noxious stimulus to a normative site on the human, wherein the noxious stimulus is applied below a pain threshold of the human.

5. The method of claim 4, wherein the first step of performing a first manipulation is conducted for about one minute.

6. The method of claim 1, wherein the first information, the second information, the third information and the fourth information each comprise at least one of: an angle of a portion or a limb of the human; an amount of pressure applied to a portion of the human; and an amount of pressure applied by a portion of the human.

7. The method of claim 6, wherein the first information, the second information, the third information and the fourth information each comprise at least one of: a degree or radian value; a first pounds-per-square-inch value; and a second pounds-per-square-inch value.

8. The method of claim 1, wherein the second step of performing a second manipulation comprises: performing a second manipulation being a second noxious stimulus to a source of the pain in the human, wherein the second noxious stimulus is applied until pain threshold is reached.

9. The method of claim 1, wherein the second step of performing a second manipulation further comprises: performing a second manipulation being a second noxious stimulus to a source of the pain in the human, wherein the second noxious stimulus is applied until pain threshold is reached by observing a reaction of the human, wherein the reaction of the human includes at least one of: a motor response; a verbal response; a vocal response; a social response; and efforts to conceal or suppress external signs of pain.

10. The method of claim 9, wherein the second step of performing a second manipulation is conducted for about five seconds.

11. The method of claim 9, wherein the step of increasing comprises: increasing the second noxious stimulus until pain tolerance is reached by observing a reaction of the human, wherein the reaction of the human includes at least one of: a motor response; a verbal response; a vocal response; a social response; and efforts to conceal or suppress external signs of pain.

12. The method of claim 11, wherein the step of increasing is conducted for about five seconds.

13. The method of claim 11, wherein the step of continuing to apply the second noxious stimulus comprises: continuing to perform said second manipulation being the second noxious stimulus until observing a reaction of the human indicating the human can no longer tolerate the second noxious stimulus, wherein the reaction of the human includes at least one of: a motor response; a verbal response; a vocal response; a social response; and efforts to conceal or suppress external signs of pain.

14. The method of claim 13, wherein the step of continuing is conducted for about five seconds.

* * * * *